(12) United States Patent
Van Der Weegen (10) Patent No.: US 6,626,826 B1
(45) Date of Patent: Sep. 30, 2003

(54) EXAMINATION DEVICE (75) Inventor: Clemens Van Der Weegen, Lidcombe (AU)

(73) Assignee: S.S.H. Medical Limited, Lidcombe (AU)

( * ) Notice: Subject to any disclaimer, the term of this patent is extended or adjusted under 35 U.S.C. 154(b) by 0 days.

(21) Appl. No.: 09/807,913

(22) PCT Filed: Oct. 20, 1999

(86) PCT No.: PCT/AU99/00902

§ 371 (c)(1),
(2), (4) Date: Jul. 20, 2001

(87) PCT Pub. No.: WO00/22974

PCT Pub. Date: Apr. 27, 2000

(30) Foreign Application Priority Data

Oct. 20, 1998 (AU) .................................. PP6626

(51) Int. Cl.[7] ................................. A61B 1/04
(52) U.S. Cl. ....................... 600/131; 600/119
(58) Field of Search ................. 600/131–142, 600/119, 105, 121; 606/46

(56) References Cited

U.S. PATENT DOCUMENTS

| 1,679,950 | A | 8/1928 | Stern |
| 3,144,020 | A | 8/1964 | Zingale |
| 3,817,251 | A | 6/1974 | Hasson |
| 4,258,721 | A | 3/1981 | Parent et al. |
| 4,593,681 | A | 6/1986 | Soni |

FOREIGN PATENT DOCUMENTS

| DE | 4404253 A1 | 8/1995 |
| WO | A9421160 | 9/1994 |
| WO | A9819590 | 5/1998 |

*Primary Examiner*—Tu Ba Hoang
(74) *Attorney, Agent, or Firm*—Birch, Stewart, Kolasch & Birch, LLP

(57) ABSTRACT

An examination device for examining the interior of a body cavity has a tubular probe having a first, forward end and a second, rearward end. The probe is mounted in a hand piece, and a closure is engaged with the second end of the probe. A shield is provided on the probe either adjacent the first end or spaced therefrom but forwardly of the hand piece to shield the hand piece from contact with body tissue. The shield is also able to seal against a body orifice.

8 Claims, 14 Drawing Sheets

FIG_2.

FIG_4.

FIG_3.

FIG_9_

FIG_10

FIG_23_

FIG_24_

FIG_25_

FIG_26.

FIG_27.

EXAMINATION DEVICE

This application is the national phase under 35 U.S.C. §371 of PCT International Application No. PCT/AU99/00902 which has an International filing date of Oct. 20, 1999, which designated the United States of America and was published in English.

TECHNICAL FIELD

This invention relates to examination devices of the kind used by physicians to examine the interiors of body cavities and/or the orifices thereof and to facilitate surgical operations within the body cavities. In particular the present invention is described with reference to an examination device for use in relation to the vagina.

BACKGROUND ART

There are a number of ways in which physicians routinely examine the interior of the vagina. One such method is to employ a known dilating speculum comprising a tubular array of two or more rigid, elongate leaves, which are inserted into the vagina of a patient and expanded in a radially outward direction to open the vagina for inspection. When prior known speculums have been used to admit pressurised fluid for expanding a body cavity having an external orifice, such as the vagina, it has been usual to tolerate the escape of some of the fluid, usually air but sometimes liquid, even though this is unpleasant for the operator and increases the messiness of the operation. Proposals to alleviate the disabilities flowing from the escape of fluid have included the use of inflatable sealing elements encircling a part of the tubular probe within the body cavity but near the orifice thereof. This has not always been effective and invariably obstructs the view of the cavity surface contacted by the sealing element. Furthermore, the provision of such sealing elements and the means to inflate them have materially increased the cost of the disposable, so called throw away, tubular probe.

Colposcopes are routinely employed by physicians to examine the interior of the vagina through such a speculum. Colposcopes typically comprise a binocular microscope and an illuminating unit which allows the physician to examine the vagina. In many instances the colposcope is a bulky and expensive instrument set on a stand at approximately 300 mm away from the vagina, and as a result of the magnification provided by the microscope the physician is able to conduct a close up examination. As the colposcope is bulky and requires a relatively large stand capable of supporting it, it is difficult for the physician to work in close to the area being examined, particularly when taking pap smears and/or conducting minor surgery.

Germany Patent Specification No. DE4404253 discloses an exploratory device which includes a sealing plug having feed through ducts for an instrument and connection ducts for a suction connection or an air supply connection to enable gas to pass into or out of the body cavity. A feature of the plug is the provision of an aspirator integral with the plug for controlled removal of gases from the body cavity being. With such an arrangement, sterilisation is difficult and an additional, inflatable seal is preferred which has the disadvantages to which reference has previously been made.

U.S. Pat. No. 3,817,251 discloses a cannula for laparoscopy which includes a cone shaped sleeve adapted to block the incisional gap. With this arrangement, the sleeve is formed of stainless steel or a chrome plated steel and is used for surgical treatment where an incision is made into the abdominal wall. This structure is totally unsuitable for use in examining the interiors of body cavities and would be difficult to seal against the cavity opening.

U.S. Pat. No. 4,258,721 relates to a hysteroscope which includes a cannula for insufflation of a fluid, such as carbon dioxide, inside the uterine cavity. The cannula is combined with an element which abuts the cervix of the uterus. However, the shape of the abutting element is such that a substantial part thereof is engaged within the opening thus preventing examination of the tissue adjacent thereto.

It is therefore desirable to provide an improved examination device which obviates at least some of the disadvantages of prior examination devices and which, in addition, is relatively simple and economical to manufacture and use.

It is also desirable to provide an examination device which is simple to use up close to a body cavity being examined, and through which biopsy samples may be obtained and surgery may be conducted with greater facility than heretofore.

SUMMARY OF INVENTION

In one aspect the present invention comprises an examination device for use in examining the interior of a body cavity, said device including an elongate tubular member having a first end and a second end, a hand piece having a bore there through, and a closure means including an eyepiece, the elongate tubular member being detachably fitted within the bore of the hand piece and the closure means being secured to the second end of the tubular member to provide a line of sight extending through the closure means and along the bore of the tubular ember, and the tubular member having a shield means which extends radially outwardly way from the tubular member for preventing contact of the hand piece and closure means with tissue surrounding the body cavity being examined.

In an embodiment of the invention, the shield means comprises an annular member removably engaged with the tubular probe to extend substantially radially therefrom. The diameter of the shield means is such that a front surface portion is able to contact tissue surrounding the opening of the body cavity being examined in such a way as to seal against the egress of fluid from the body cavity.

Preferably, the hand piece includes a light source from which light may be transmitted through the tubular probe, which, in this embodiment, is of a material capable of transmitting light.

In another embodiment the shield means is a cup or dome shaped member which, in use, is adapted to overlie and partially surround at least a part of the hand piece. The cup or dome shaped shield member has a base portion by which the shield member is engaged with the tubular probe. The base portion has an outer surface adapted to engage and seal with tissue surrounding the opening of the body cavity. One or more annular ribs or like surface deformations may be formed in the outer surface of the base portion to enhance the sealing with the surrounding tissue.

Embodiments of the invention may provide means for admission of a pressurised fluid into the bore of said tubular probe for expanding the body cavity. In such embodiments, the closure means is provided with a self-sealing aperture for the insertion through the tubular probe and into the expanded body cavity of surgical instruments, such as catheters, tissue sample extractors, cauterising devices and the like. The shield means of the present invention facilitates the use of such devices by reducing the escape of fluid from the expanded body cavity during the examination and subsequent procedure.

In a further embodiment of the present invention, the shield means comprises a disposable, annular shield sealingly engaged with the tubular probe and extending radially therefrom. The shield is configured and dimensioned to provide a surface portion of substantial area to contact an area of body tissue surrounding the orifice of the body cavity to be examined. The shield is formed of a resilient deformable material and may be provided with one or more annular ribs or the like to enhance sealing contact with the body tissue. The shield may be of disc shaped, dome or cup shaped or bell shaped so as to partially fit within the orifice of the body cavity whilst having a side wall which shields the hand piece. By forming the shield of a resilient, deformable material, use of the shield does not result in discomfort to the patient and provides a degree of movement of the tubular probe by an operator as the probe is directed towards different parts of the internal cavity surface to be examined or treated, without losing sealing efficiency of the shield. Further, the resilient, deformable shield is easily and quickly assembled with a tubular probe in a sealing manner and in a way which ensures that the shield is retained in place on the tubular probe and effects a fluid seal with the probe.

In one form of the invention, the tubular probe is provided with a circumferential abutment on an external surface thereof a predetermined distance from is first end. The shield, which has a substantially centrally located opening therein, is a sliding, interference fit with the first end of the tubular probe and abuts the circumferential abutment to locate the shield axially along the tubular probe and providing an increased sealing effect between the surfaces of the shield and the tubular probe. In a particular form of the invention, the shield is moulded from a closed cell, resilient plastics foam material or is cut or stamped or otherwise formed from a sheet of such material. A suitable synthetic plastics material includes polyethylene but may also include any other plastics material capable of forming a resilient closed cell body having smooth external surfaces which are impervious to gas or liquid penetration and which is resistant to chemical reaction with body fluids, sterilising fluids, antiseptics and the like. In an alternative arrangement, the shield may be formed of two or more materials, such as a relatively rigid backing piece having a resilient sealing layer associated therewith.

DESCRIPTION OF THE DRAWINGS

Embodiments of the invention are described in more detail hereinafter with reference to the accompanying drawings.

DESCRIPTION OF PREFERRED EMBODIMENTS

FIGS. 1 to 8 depict a first embodiment of an examination device intended for use in the examination of the vagina. The device comprises an elongate tubular probe 1, a hand piece 2 and a closure member 3.

Figure 1:
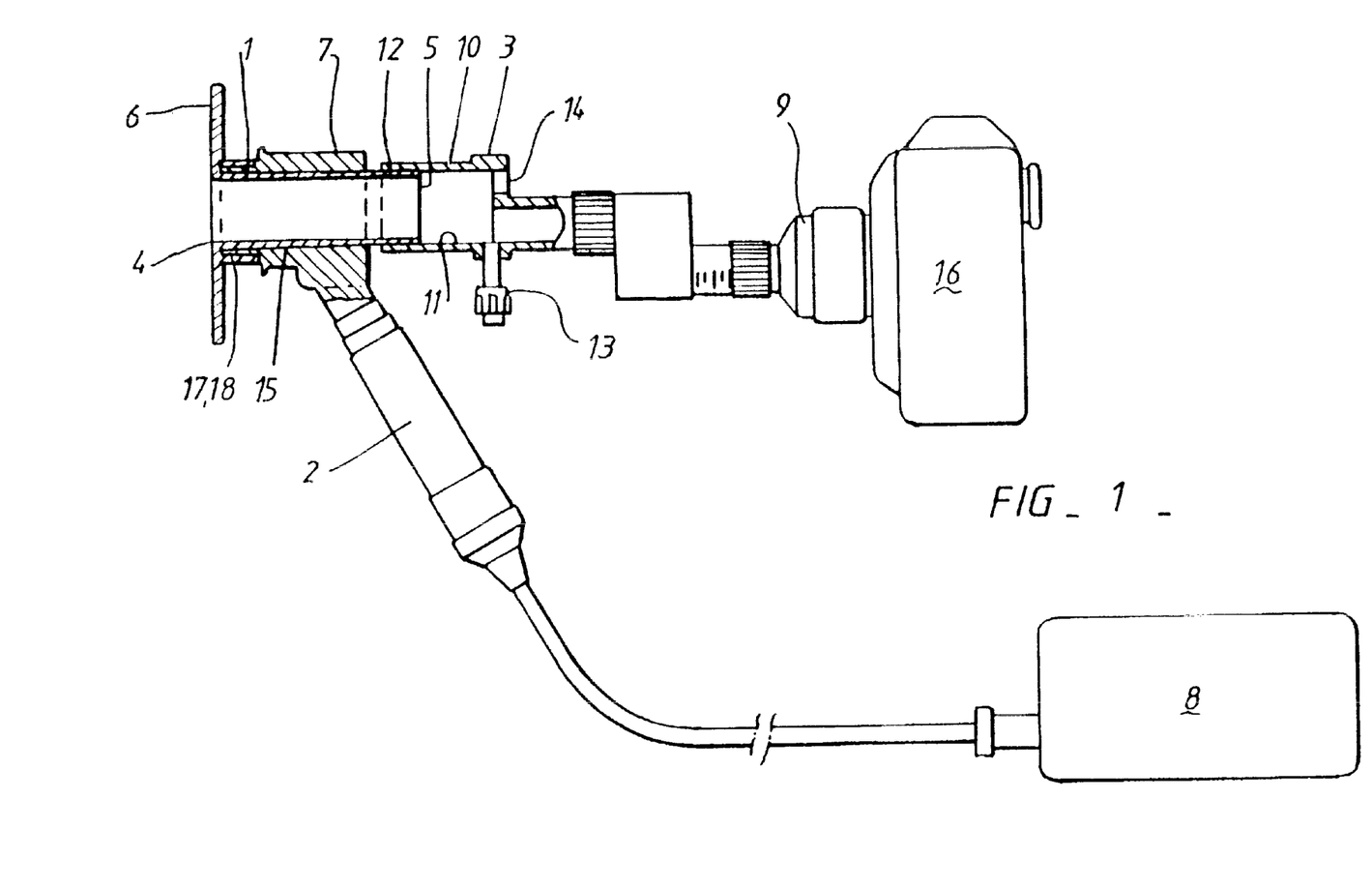
FIG. 1 is an elevational view incorporating a partial sectional view of a first embodiment of the examination device of the present invention.
Figure 5:
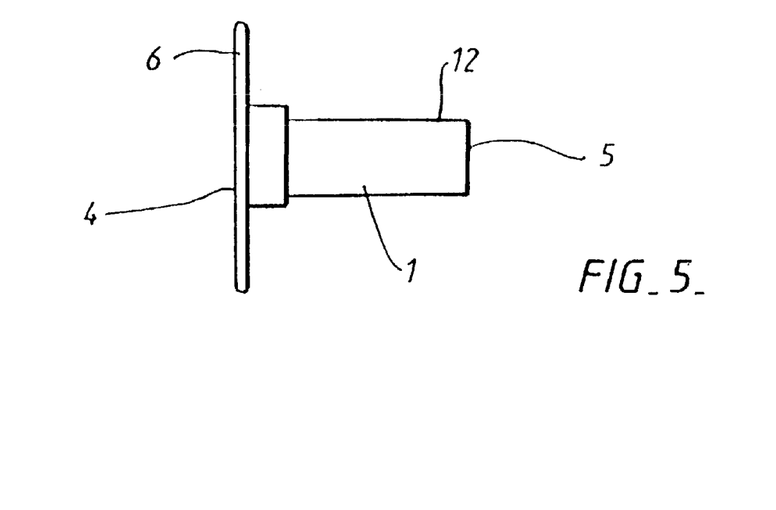
FIG. 5 is an elevational view of an elongate tubular probe of the device shown in FIG. 1 incorporating a shield according to the invention.
Figure 6:
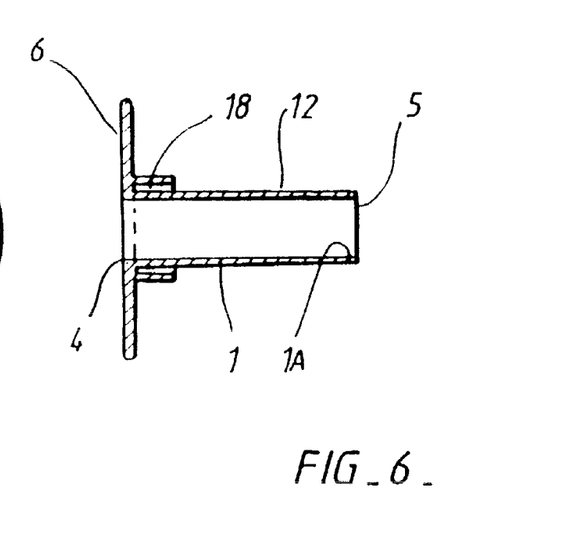
FIG. 6 is a longitudinal sectional view of the tubular probe shown in FIG. 5.
Figure 7:
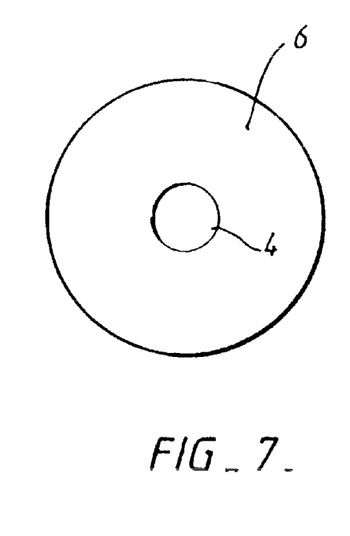
FIG. 7 is a front end view of the tubular probe shown in FIG. 5.
Figure 8:
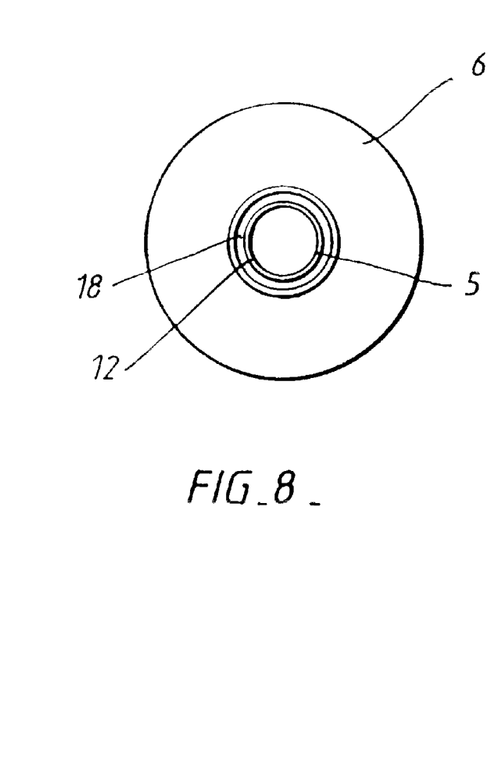
FIG. 8 is a rear end view of the tubular probe shown in FIG. 5.

Tubular probe 1 is a colourless transparent plastic moulding which may, for example, be of acrylic having a bore 1A therethrough. For ease of reference, tubular probe 1 can be described as having a first end 4 and a second end 5. A shield or guard means 6 of a larger diameter than the body of the tubular probe 1 is located at the first end 4.

The shield 6 is a disc like member which may be integral with the first end 4 of the tubular probe 1, in which case it is formed of the same material as the tubular probe 1, or it may be a separate member which is secured to the tubular probe 1. The shield 6 has a front surface 6A which is adapted to sealing engage tissue surrounding the body cavity opening to be examined. The diameter of the shield 6 is such as to engage tissue externally of the opening.

The hand piece 2 has a support sleeve 7 integral therewith, and contains a light source (not shown) therein. In this embodiment the handle is connected to a transformer (light box) 8 which provides a low voltage power source of say 3–12 volts to power the light source contained within the handle 2. Alternatively, self-contained batteries may be used. The sleeve 7 has a bore 15 therethrough which is adapted to allow the tubular probe 1 to be removably fitted therein in such a manner that the shield 6 at the first end 4 of the tubular probe 1 is at the front of hand piece 2, as shown in FIG. 1. When fitted, the front end 17 of the sleeve 7 is seated within the annular recess 18 of the tubular probe 1.

Figure 2:
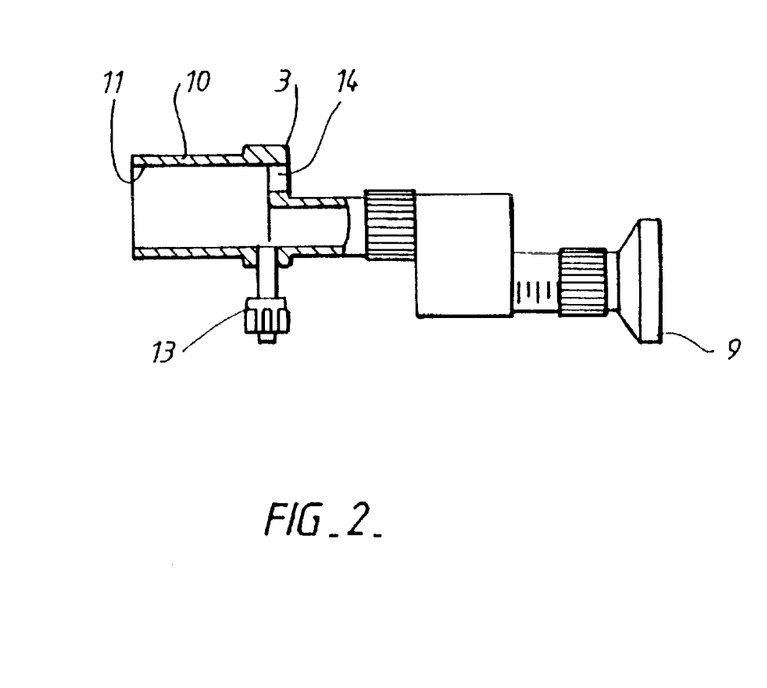
FIG. 2 is an elevational view incorporating a partial longitudinal sectional view of the closure means of the device shown in FIG. 1.
Figure 3:
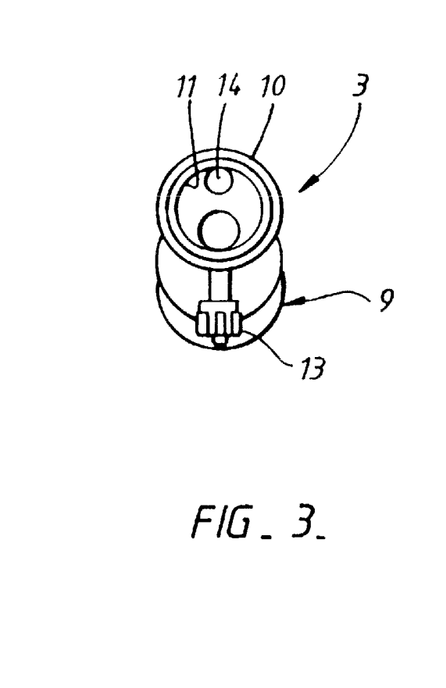
FIG. 3 is a front end view of the closure means shown in FIG. 2.
Figure 4:
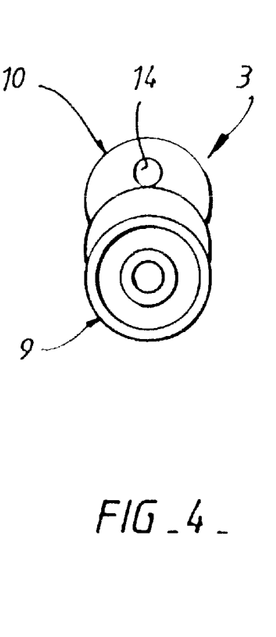
FIG. 4 is an rear end view of the closure means shown in FIG. 2.

The closure 3, has an eyepiece member 9 projecting from a sleeve portion 10, and is adapted to sealingly engage over second end 5 of the tubular probe 1. A bore surface 11 of sleeve portion 10 contacts the outer surface 12 of tubular probe 1 when closure 3 is in engagement therewith. Closure means 3 has an opening 13 adapted to be connected to one end of an air supply means (not shown) which may be a manually operated dilation bulb which allows air to be pumped into a bore of the closure 3 and into a bore of tubular probe 1. Closure 3 also has a sealable entry port 14 for insertion of a surgical implement or sampling device through the closure 3 and the tubular probe 1. When a surgical implement is not being used in conjunction with the device, the port 14 is sealed by a plug (not shown).

The examination device is usually supplied to a user as the three separate unassembled components of the tubular probe 1, hand piece 2 and closure 3. The device may be assembled for use by attaching the tubular probe 1 to the hand piece 2 by inserting the elongate tubular probe 1 through the bore 15 of the sleeve 7. The closure 3 is then fitted to the second end of tubular probe 1.

In this embodiment of the device, once the components have been assembled the shield 6 of the tubular probe 1 is at the front end of the examination device. A physician wishing to examine a vagina through a speculum, may bring the first end 4 of tubular probe 1 towards the opening of the vagina. The physician utilises the eyepiece 9, which incorporates a magnification means, to view the vagina through the device. Light from the light source contained within handle 2 is projected through the sleeve 7 and is transmitted through the colourless transparent plastic of tubular probe 1, thereby providing a light beam projected into the vagina being examined. In the present embodiment a camera 16 is shown fitted to the eyepiece 9, in order to allow the physician to take a record of the examination. It should however be understood that the device can be used without the camera 16 being fitted, and in this instance the physician would be viewing directly into the eyepiece 9.

The surgical entry port 14 in closure member 3 allows for sampling devices or surgical instruments to be passed through the device and into the vagina for taking samples or conducting minor surgery. An advantage of such an arrangement is that the physician therefore can manipulate such sampling or surgical devices from the rear of the device and his/her hands do not block the field of vision, as is sometimes the case when using known colposcopes. Furthermore, the examining device is easy to manipulate and can be readily packed away in a small case for portability. Where surgical and sampling devices are to be passed through port 14, a liner (not shown) of a disposable type may be fitted to port 14, to prevent contamination of closure means 3.

The tubular probe 1 is preferably a disposable item which may be supplied in a sterile package for use by a physician at the time of inspection. The disc like shield 6 has the purpose of providing a shield between the area being examined and that of the hand piece 2 and closure 3 in order to prevent contamination of the latter components. It will be understood that the shield means 6 may differ in configuration to that shown in FIG. 1 and may be of a larger diameter, and may for instance have a different shape such as a dome or cup like configuration, as discussed in later embodiments.

It should also be understood that a probe tip (not shown) may be fitted to the first end 4 of tubular probe 1, or alternatively may be integral with the tubular probe.

Figure 9:
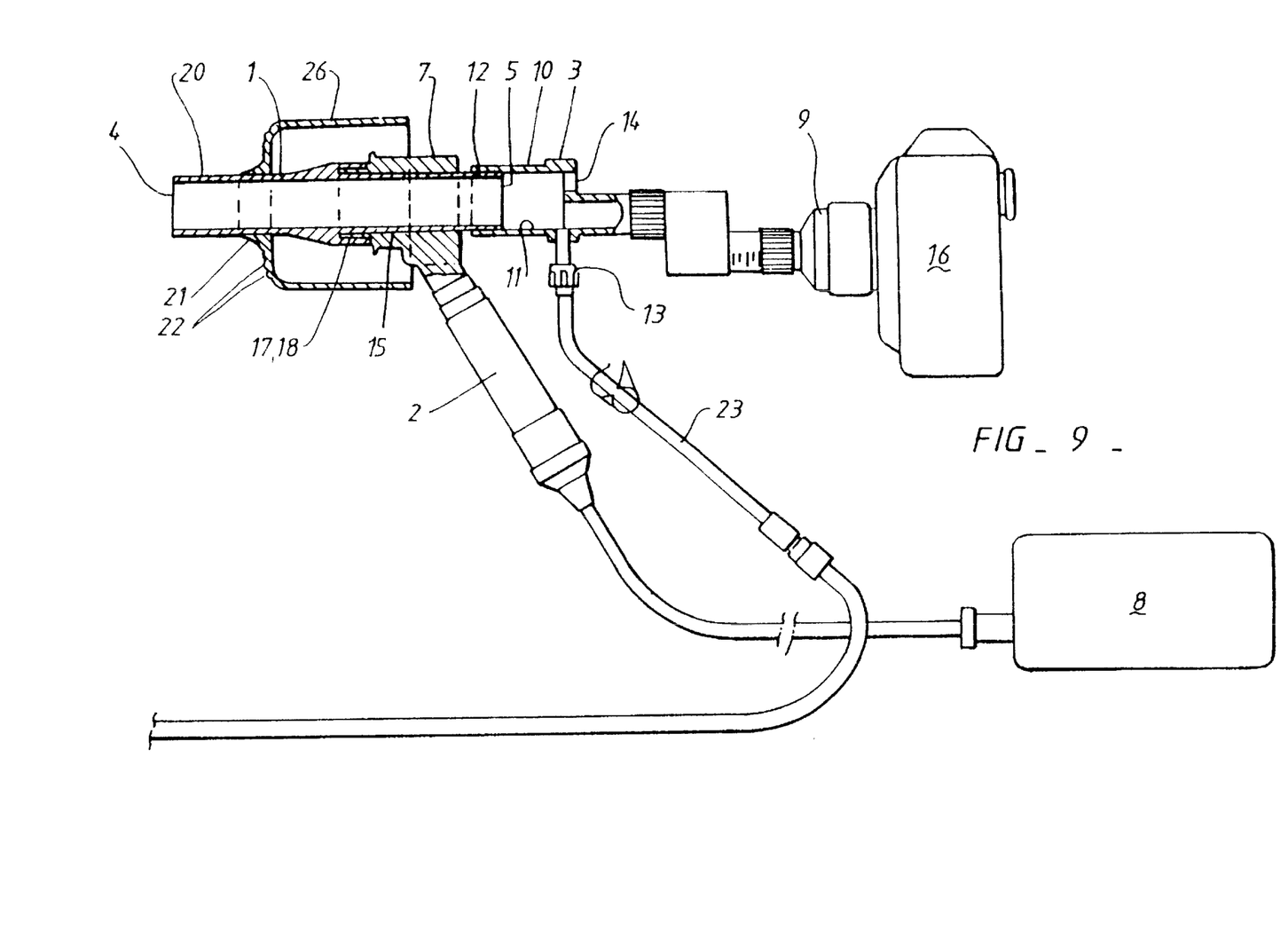
FIG. 9 is an elevational view incorporating a partial sectional view of a second embodiment of an examination device of the present invention.

FIG. 9 depicts a second embodiment of an examination device intended for use in the examination of the vagina. It has a number of like components to that of the first embodiment and such like components of the second embodiment have been numbered with the same reference numerals as used for the first embodiment.

The second embodiment of the examination device comprises an elongate tubular probe 1, a hand piece 2 and a closure member 3. The main difference between the second embodiment and that of the first embodiment, is that the disc like shield 6 is replaced by a shield 26 which is cup-shaped and is spaced from the first end 4 of the tubular probe 1. The cup-shaped shield 26 provides enhanced shielding of the sleeve 7 of the hand piece 2, and additionally allows for the examination device to be utilised as a speculum, with the portion of elongate tubular probe 1 located between the first end 4 and shield means 26 forming a probe 20 for insertion into a vagina In use, the probe 20, is inserted into a vagina and passes through the PC muscles, with the base 21 of the shield 26 pushed against the periphery of the vaginal opening. The base 21 of the shield 26 is provided with a number of annular ribs 22. Once the probe 20 has been inserted into the vagina and the ribs 22 of the shield 26 have been pushed up against the periphery of the vaginal opening, air can be introduced through the bore of the tubular probe 1 and into the inner cavity of the vagina by means of an air supply means connected to opening 13 on the closure 3. A delivery tube 23, which may be connected to a manually operated dilation bulb (not shown), or alternatively to a foot actuated dilation bulb, is used to deliver air to the opening 13. By holding the shield 26 against the outer body at the vaginal opening, a seal is maintained to ensure that the air introduced into the inner cavity of the vagina does not escape. This enables the user to inspect the vagina through eye piece 9. The inspection of the inner cavity of the vagina is possible as the closure means 3 incorporates eye piece 9 with a line of sight extending through the bore of the tubular probe 1.

The design of this second embodiment of the present invention, is such that the shield means 26 allows for the examination device to be moved at the entrance of the vagina to conduct a thorough examination of the inner cavity, which is assisted by having air expand the vagina.

Figure 10:
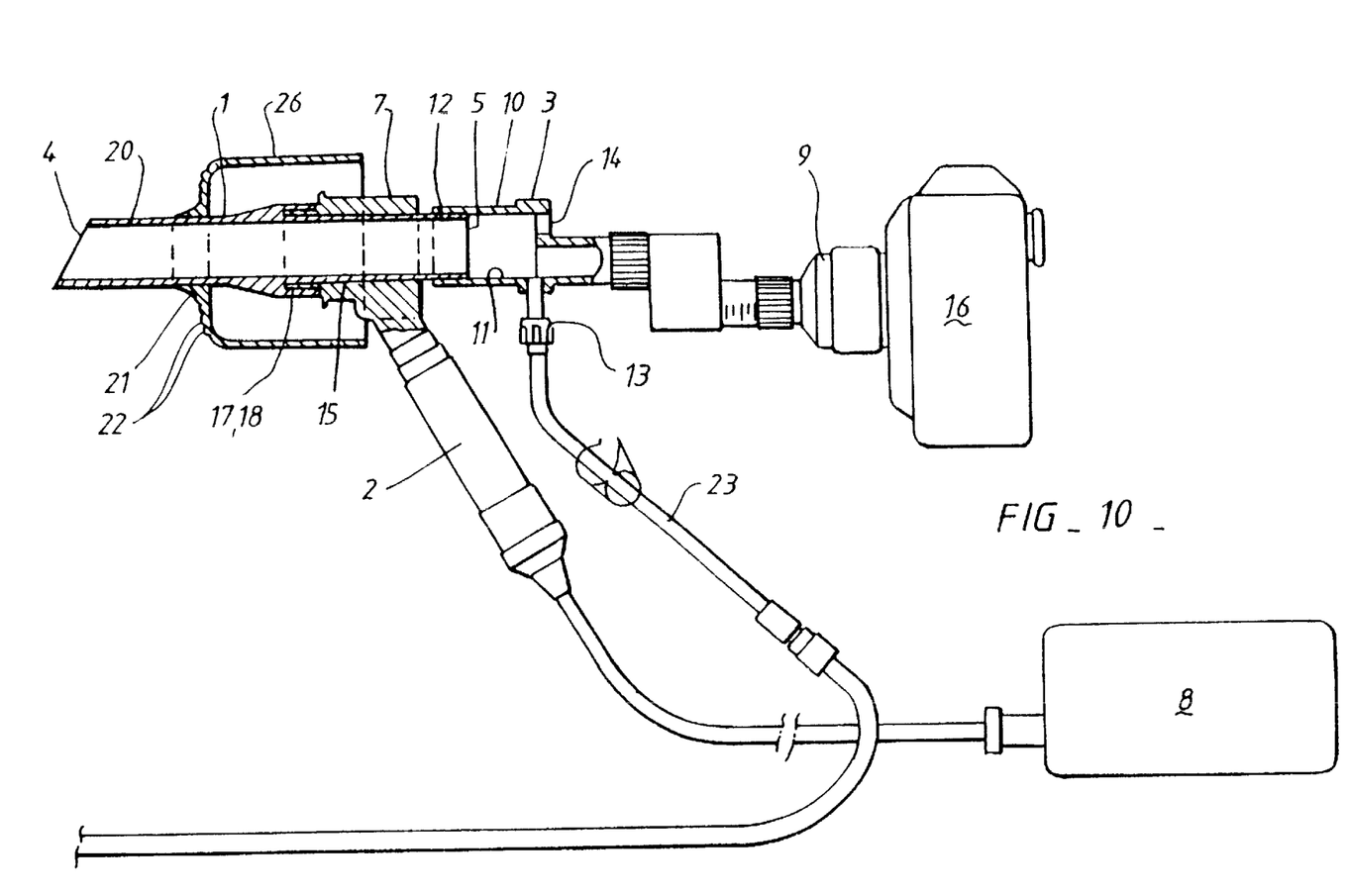
FIG. 10 is an elevational view incorporating a partial sectional view of a third embodiment of an examination device of the present invention.

FIG. 10 illustrates a third embodiment of a examination device in accordance with the invention. In this embodiment, first end 4 is oblique to the longitudinal axis of the tubular probe, such that the light being transmitted therefrom can be positionally controlled by rotating the examination device whilst probe 20 is inserted in the inner cavity of the vagina.

Figure 11:
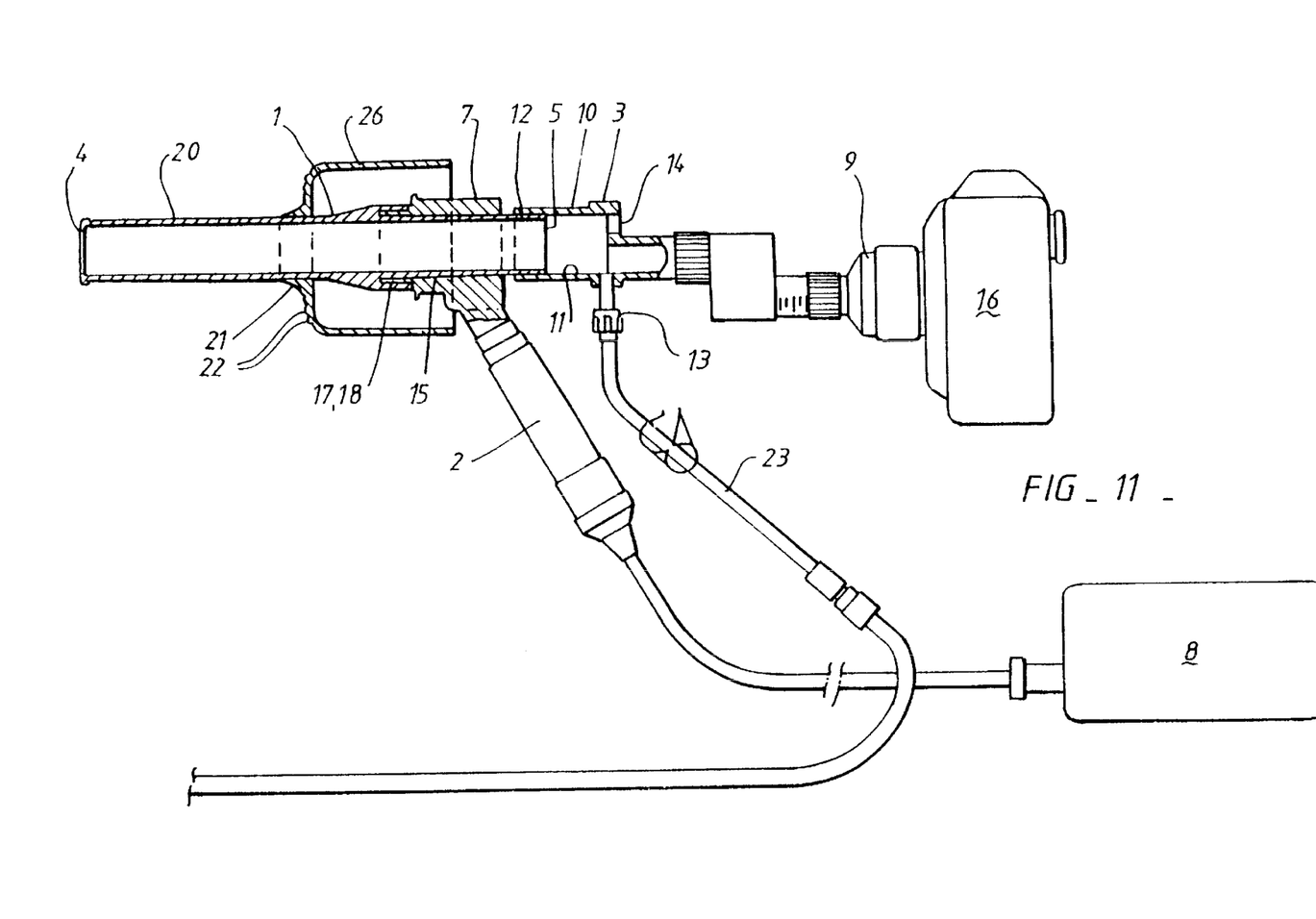
FIG. 11 is an elevational view incorporating a partial sectional view of a fourth embodiment of an examination device of the present invention.

It will be understood that the dimensions of the tubular probe 1 and of the shield 26 may vary in accordance with needs of different patients and different types of examination. Thus, both the diameter of the shield 26 and the length of the probe portion 20 will change. In a fourth embodiment as shown in FIG. 11, an examination device similar to that of the second embodiment is shown, the main difference being the probe 20 is longer. In situations where a tissue or culture sample is to be taken from the cervix the user, having located the cervix, may press the free end 4 of tubular probe 1 of this fourth embodiment against the cervix, then remove closure 3. A sample may then be obtained by inserting a spatula through the tubular probe 1 to scrap the necessary cellular material. Alternatively, a spatula or cervical brush (not shown) may be inserted into the bore of the tubular probe 1 prior to insertion of the probe 20 of the examination device into the inner cavity of the vagina. The spatula or cervical brush may be manipulated by a manipulatable end which passes through the port 14 in the closure 3. A ring 27 (see FIG. 12) at the first end 4 of the tubular probe of this fourth embodiment is provided as an abutment for the head of the spatula (or cervical brush) whilst the probe and spatula are inserted into the vagina.

Figure 12:
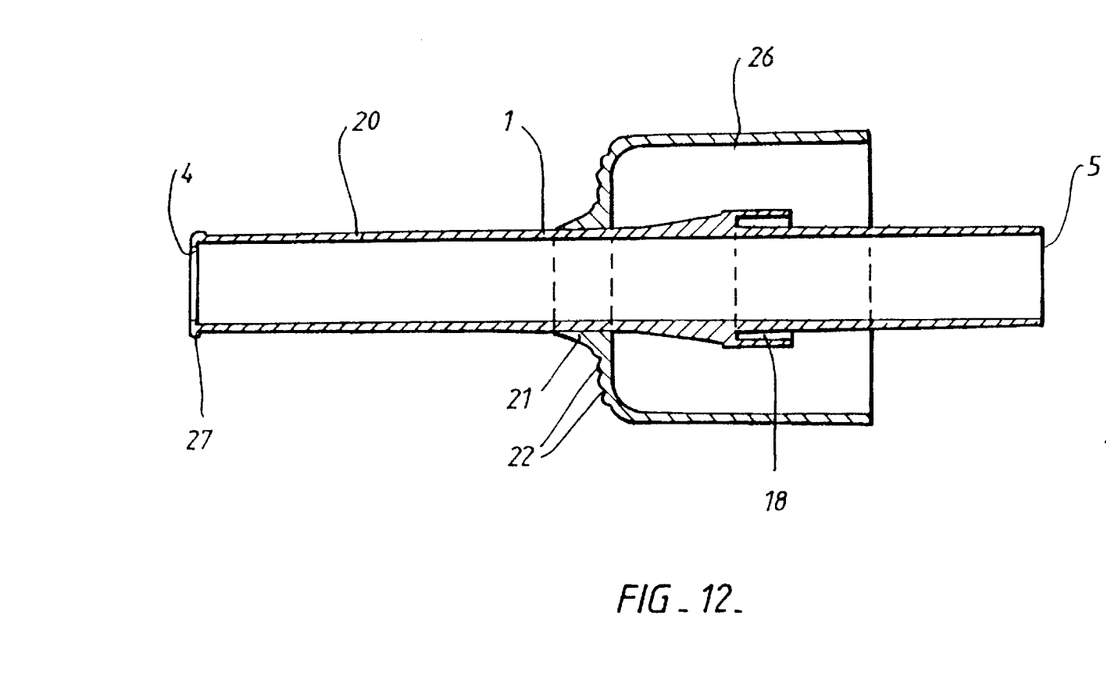
FIG. 12 is an enlarged cross sectional view of the tubular probe and shield means depicted in FIG. 11.
Figure 13:
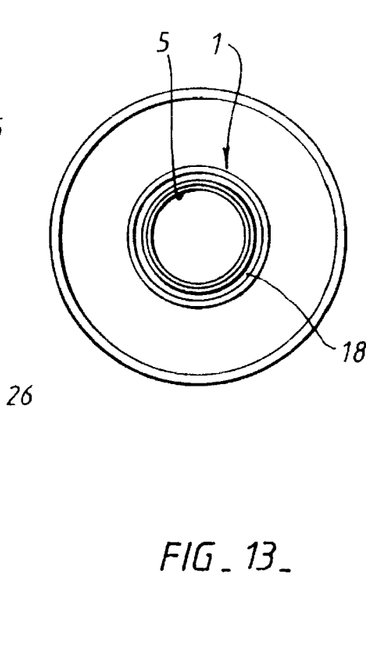
FIG. 13 is an enlarged end view of tubular probe and shield means shown in FIG. 12.
Figure 14:
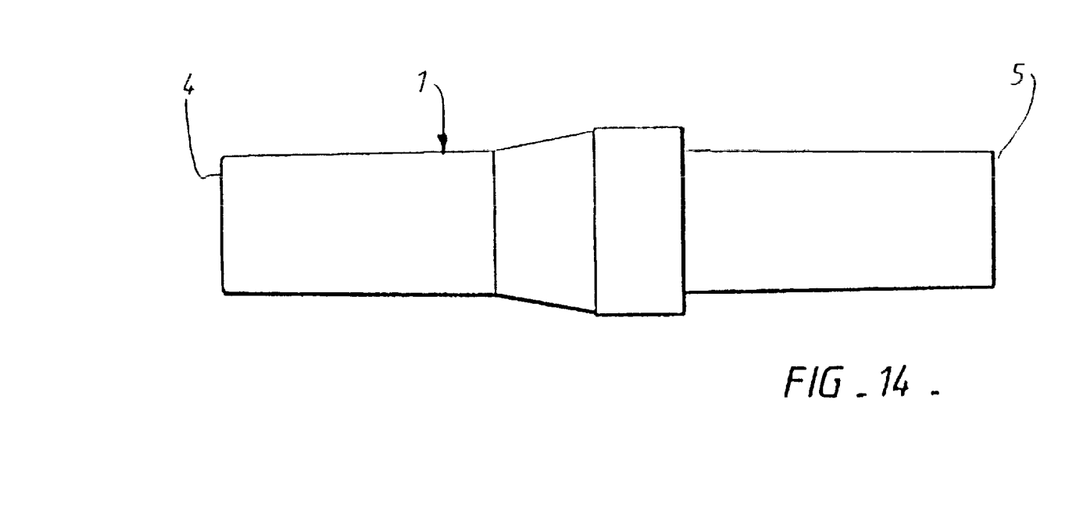
FIG. 14 is an enlarged elevational view of the tubular probe of the second embodiment of the examination device shown in FIG. 9.
Figure 15:
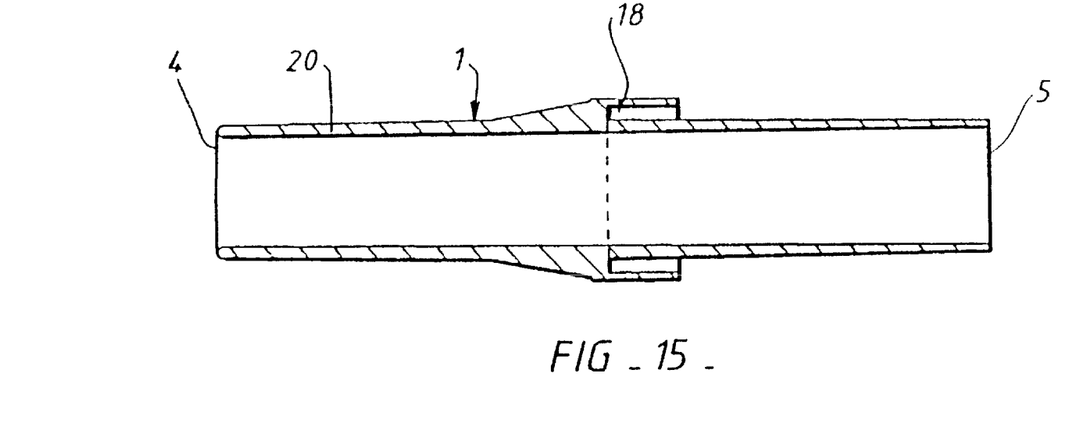
FIG. 15 is a cross-sectional view of the tubular probe shown in FIG. 14.
Figure 16:
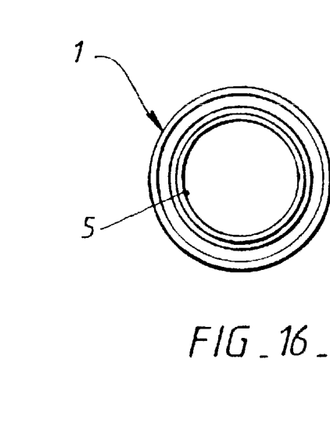
FIG. 16 is an end view of the tubular probe shown in FIG. 14.
Figure 17:
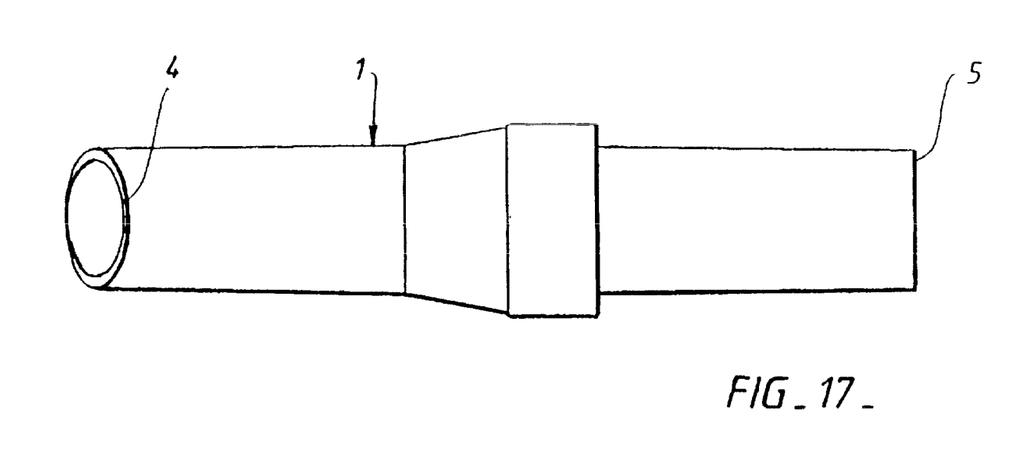
FIG. 17 is an enlarged elevational view of the tubular probe of the third embodiment of the examination device shown in FIG. 10.
Figure 18:
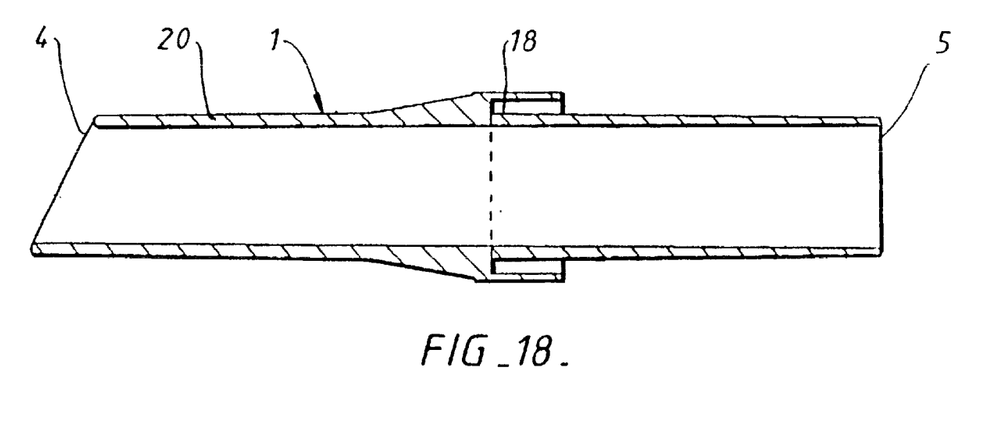
FIG. 18 is a cross-sectional view of the tubular probe shown in FIG. 17.
Figure 19:
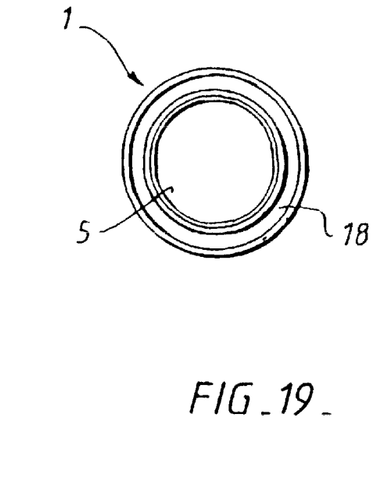
FIG. 19 is an end view of the tubular probe shown in FIG. 17.
Figure 20:
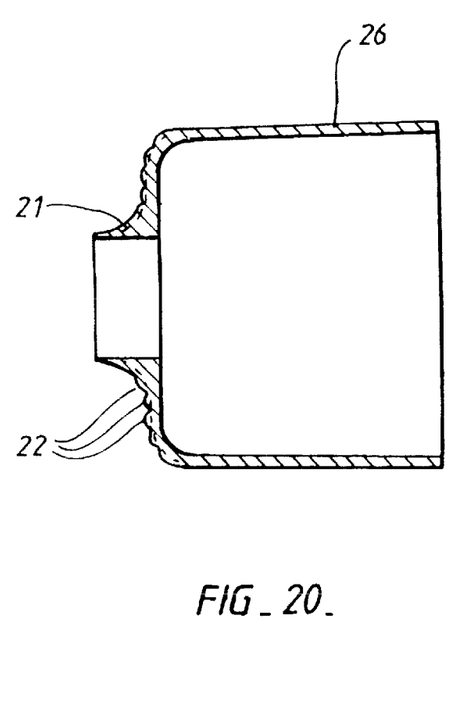
FIG. 20 is an enlarged cross-sectional view of the shield means shown in FIGS. 9, 10 and 11.
Figure 21:
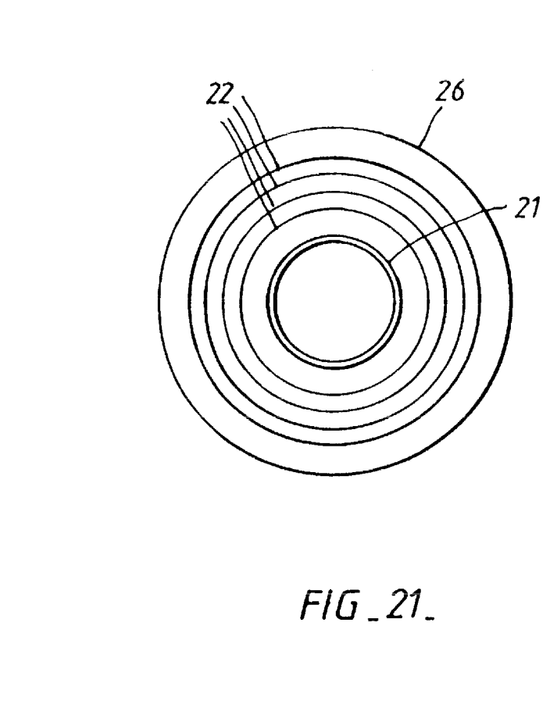
FIG. 21 is a front end view of the shield means shown in FIG. 20.
Figure 22:
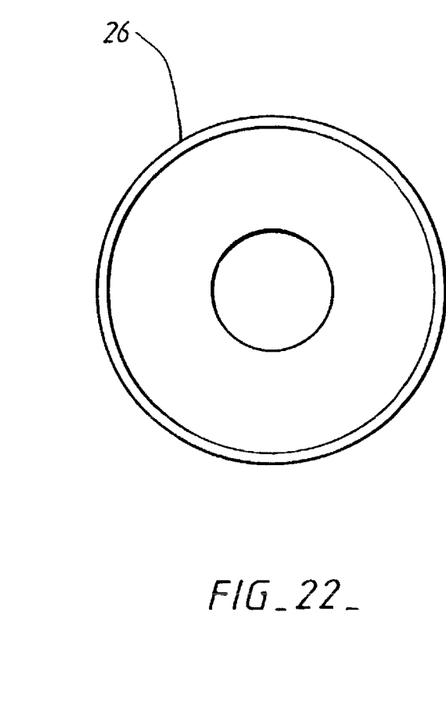
FIG. 22 is a rear end view of the shield means shown in FIG. 20.

FIGS. 12 and 13 shown an enlarged detail of the tubular probe 1 and shield 26 of the fourth embodiment. It will be understood that these may be separate components made of disposable synthetic plastic material and may be assembled so that the shield 26 sealing engages on the tubular probe 1. The tubular probe 1 of the second and third embodiments are shown in enlarged detail in FIGS. 14–16 and FIGS. 17–19, respectively, whilst the cup-shaped shield 26 is shown in FIGS. 20–22. It should be understood that the shield 26 of FIG. 20 may be fitted and secured to either of the tubular probes 1 shown in FIG. 15 or 18 by means of a Morse taper.

Figure 23:
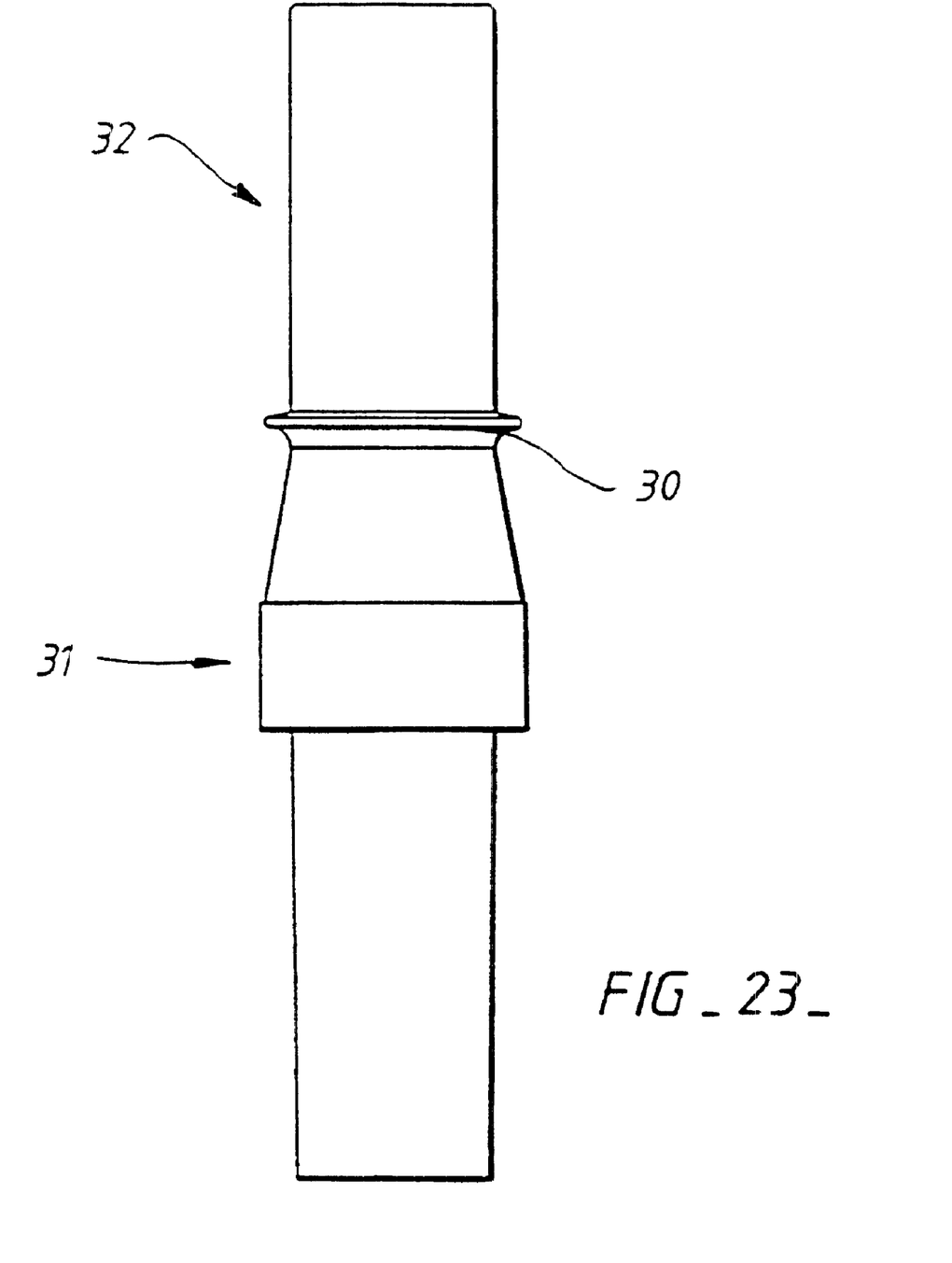
FIG. 23 is side elevation of a tubular probe, being a disposable component of a fifth embodiment of an examination device of the invention.
Figure 24:
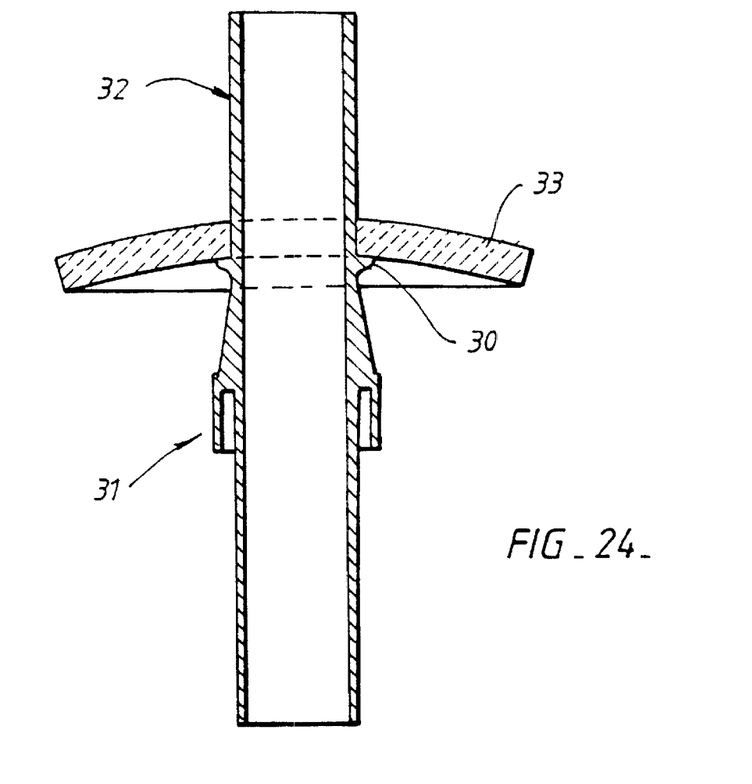
FIG. 24 is a longitudinal sectional elevation of a tubular probe and sealing means of the fifth embodiment including the probe of FIG. 23.
Figure 25:
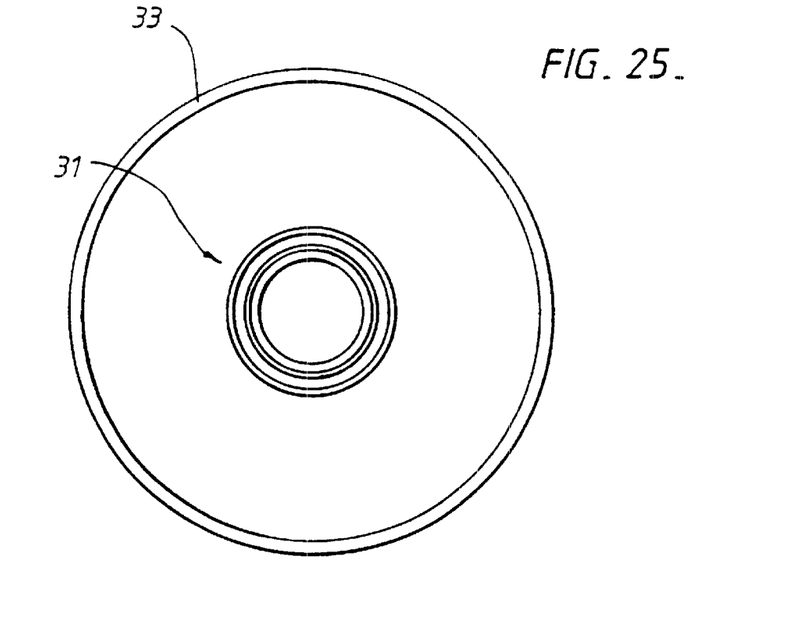
FIG. 25 is an end elevation of the embodiment of FIG. 24.
Figure 26:
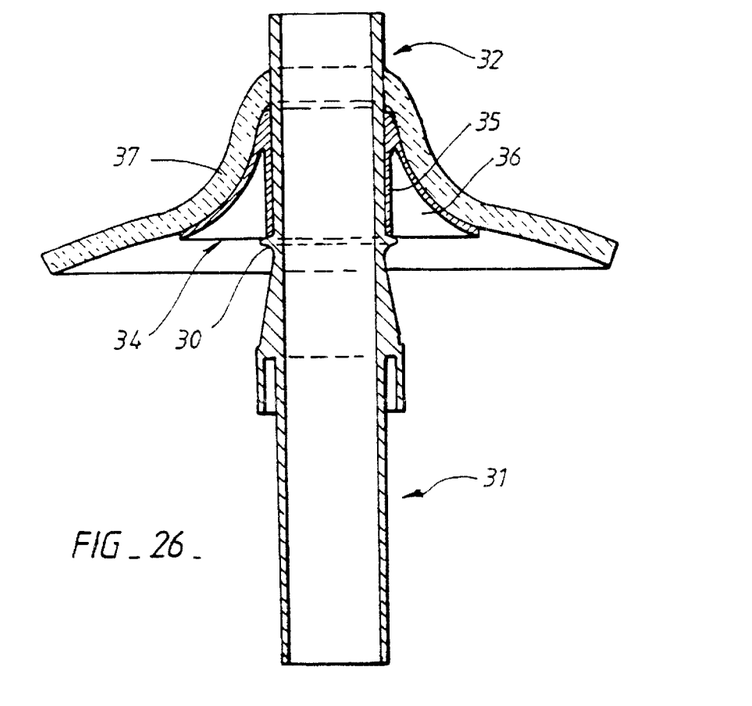
FIG. 26 is a view similar to FIG. 24 of a tubular probe and sealing means of a sixth embodiment of an examination device of the invention.
Figure 27:
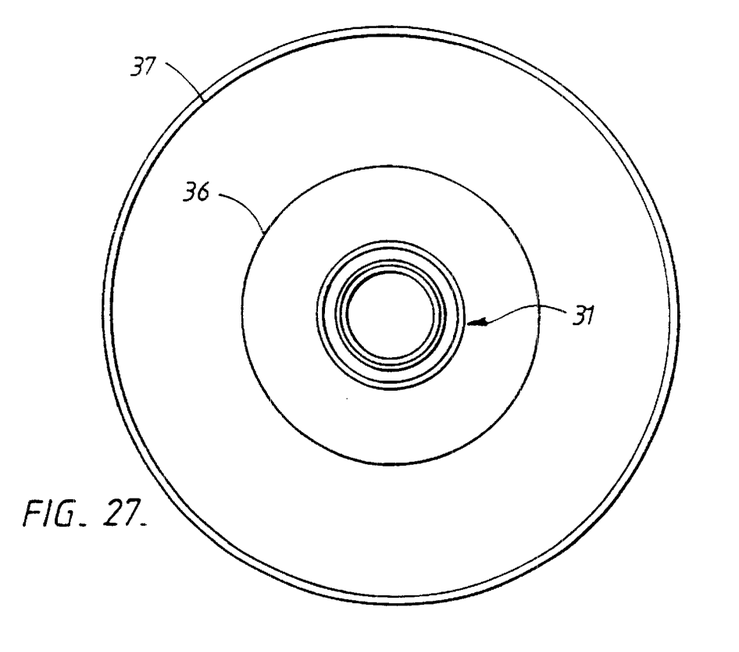
FIG. 27 is an end view of the probe and sealing means of FIG. 26.
Figure 28:
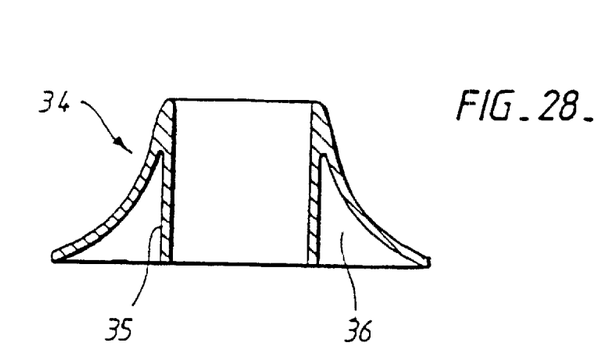
FIG. 28 is a longitudinal sectional view of a backing piece appearing in FIG. 27.
Figure 29:
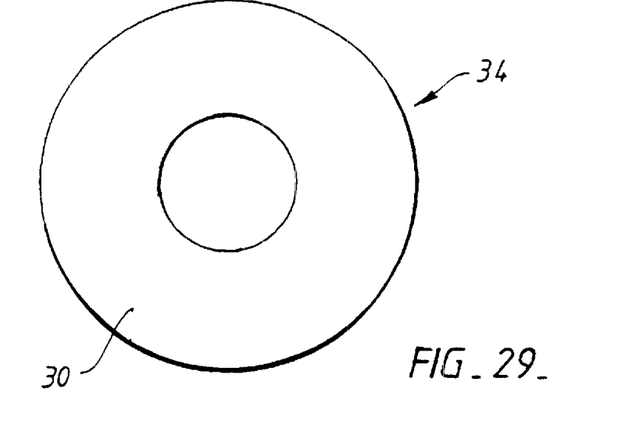
FIG. 29 is front end view of the backing piece of FIG. 28.
Figure 30:
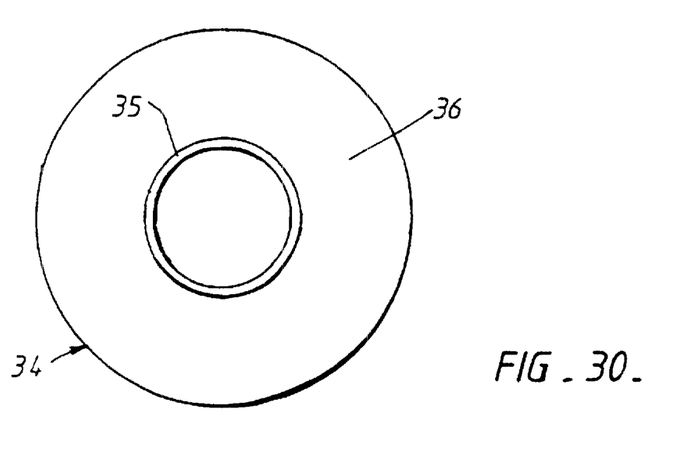
FIG. 30 is a rear end view of the backing piece of FIG. 28.

The tubular probe shown in FIGS. 23 to 25 is essentially the same as the probe of the earlier described embodiments except for the presence of a circumferential abutment 30 thereon. The portion 31 of the probe to the rear of the abutment 30 is configured to receive a hand piece and a closure in the same manner as in the previous embodiments. Similarly, the probe portion 32 ahead of the abutment 30 is adapted to enter a body cavity in such a manner and for the same purpose as the tubular probes of the preceding embodiments.

The abutment 30 acts as a locating shoulder for a combined shield and sealing element 33. The element 33 comprises a domed, self supporting, annular layer of foamed synthetic plastics material, such as polyethylene which is sufficiently resilient to be relatively soft to the touch but with sufficient stiffness to be able to act as a seal.

In the embodiment illustrated in FIGS. 26 to 30, the shield comprises a relatively stiff backing element 34 comprising a tubular core 35 adapted to engage as sleeve on the front end portion 32 of the tubular probe. The tubular core 35 contacts the abutment 30 to locate the core and backing element in position. The element includes a flared skirt 36 extending from the forward end of the core 35.

The backing element 34 supports the centre portion of a L-shaped annular shield 37 which sealingly engages the surface of the tubular probe at the forward end portion 32 in front of the tubular core 35. The shield 37 is preferably moulded of a foamed synthetic plastics material having a resiliency to be relatively soft to the touch but being sufficiently stiff as to be self-supporting outwardly of the backing element 34 so as to be able to be seal against body tissue surrounding the orifice into which the probe is inserted. If desired, sealing ribs or the like may be moulded into the front surface of the element 37 to assist the sealing action when engaged with the body tissue. The close engagement of the element 37 with the forward end 32 of the probe ensures an effective seal between the element 37 and the probe as well as frictionally retaining the shield in place in use.

An advantage of the described embodiments of the present invention is that the examination device can be used in conjunction with a known dilating speculum for inspection of the vagina, or by itself, as in the second, third and fourth embodiments to conduct an examination of the vagina by introducing air therein. When used by itself, without use of dilating speculum, a further advantage is that the risk of contamination of the cervix by a lubricant such as is typically used with speculums, is substantially reduced.

When an examination and/or surgical procedure is complete, the tubular probe 1, the shield 6, 26 and any other disposable component may be discarded, and new disposable components used for a next examination.

It will be apparent that while the tubular probe 1, is described as being formed from a plastics material such as acrylic, which is substantially rigid, it may also manufactured from a plastics material which has a greater flexibility, or from some other material such as silicone rubber or the like.

In other shown variations of the second, third and fourth embodiments, the ribs 22 on the shield 26 may be replaced by other forms of surface deformations which act as a seal when engaged with body tissue. Alternatively, an elasticised annular seal member, possibly of silicone rubber or the like, may be fitted against the base 21 to provide the seal. Such a seal member may of solid or resilient material or, alternatively, may be in the nature of a pliable bag having an enclosed cavity containing fluid such as air or water.

In another embodiment not illustrated the cup-shaped shield 26 as shown in the second, third and fourth embodiments may be reversed on the tubular probe 1 such that, in use, the open end of the cup engages with the tissue surrounding the opening of the body cavity when the probe 20 is inserted thereinto.

The examination device of the above described embodiments may be supported by a stand or other support member when in use. Preferably the hand piece of the device would engage with the stand.

Although described above primarily with reference to examination of the vagina, it will be appreciated that the examination device according to the invention, but modified if necessary in respect of the relative size and shape of the tubular probe and the shield, may be used for internal examination of other body cavities, for example the lower bowel, ear, nose or throat or, for veterinary use, the body cavities of animals.

In other embodiments the ring shaped abutment 30 may be replaced by a plurality of spaced abutment lugs or may be formed as a shoulder between different diameter portions 31 and 32 of the probe.

What is claimed is:

1. An examination device for examining the interior of a body cavity, said device including a tubular probe having a first, forward end and a second, rearward end, the tubular probe being adapted to be engaged with a hand piece by which the probe is manipulated, and a sealing shield on said tubular probe adapted to shield said hand piece from contact with tissues surrounding the body cavity and further adapted to act as a seal for the body cavity to reduce egress of fluid therefrom.

2. A device according to claim 1 wherein a closure means is attached to the second end of the tubular member, the closure means including an eye-piece and being so disposed on the tubular member as to provide a line of sight therethrough.

3. A device according to claim 1 wherein said sealing shield is disc-shaped.

4. A device according to claim 1 wherein said sealing shield is cup-shaped.

5. A device according to claim 1 wherein said sealing shield is dome-shaped.

6. A device according to claim 1 wherein said sealing shield is bell-shaped.

7. A device according to claim 1 wherein said sealing shield has coaxial circular ribs or projections formed on a front surface.

8. A device according to claim 1 wherein said shield is formed of a foamed synthetic plastics material.

* * * * *